United States Patent
Lu et al.

(10) Patent No.: US 9,442,068 B2
(45) Date of Patent: Sep. 13, 2016

(54) DEVICE AND A METHOD FOR DETECTING A TRANSMITTIVITY SPECTRUM OF A LIGHT GUIDING PLATE

(71) Applicants: BOE Technology Group Co., Ltd., Beijing (CN); Beijing BOE Display Technology Co., Ltd., Beijing (CN)

(72) Inventors: Kun Lu, Beijing (CN); Kai Yan, Beijing (CN); Hetao Wang, Beijing (CN); Zhi Li, Beijing (CN); Zhanchang Bu, Beijing (CN)

(73) Assignees: BOE TECHNOLOGY GROUP CO., LTD., Beijing (CN); BEIJING BOE DISPLAY TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 13/953,007

(22) Filed: Jul. 29, 2013

(65) Prior Publication Data
US 2014/0049778 A1 Feb. 20, 2014

(30) Foreign Application Priority Data

Aug. 16, 2012 (CN) .......................... 2012 1 0293346

(51) Int. Cl.
*G01N 21/00* (2006.01)
*G01N 21/59* (2006.01)
*G01N 21/03* (2006.01)

(52) U.S. Cl.
CPC .......... *G01N 21/59* (2013.01); *G01N 21/0303* (2013.01)

(58) Field of Classification Search
CPC .. G01N 21/59; G01N 21/958; G01N 21/896; G01N 21/8806; G01N 2021/9513

USPC ......... 356/237.1–237.5, 239.1, 239.2, 239.8; 349/1, 187, 193

See application file for complete search history.

(56) References Cited

U.S. PATENT DOCUMENTS

| | | | |
|---|---|---|---|
| 3,947,131 A * | 3/1976 | Karl | 356/445 |
| 4,953,063 A | 8/1990 | Nino | |
| 5,339,093 A * | 8/1994 | Kumagai et al. | 345/89 |
| 5,764,209 A * | 6/1998 | Hawthorne et al. | 345/87 |
| 6,226,080 B1 * | 5/2001 | Takeuchi et al. | 356/239.1 |
| 6,606,116 B1 * | 8/2003 | Poynter | 348/189 |

(Continued)

FOREIGN PATENT DOCUMENTS

| | | |
|---|---|---|
| CN | 102337099 A | 2/2012 |
| JP | 401189549 A * | 7/1989 |

(Continued)

OTHER PUBLICATIONS

First Office Action issued by State Intellectual Property Office of the People's Republic of China for Chinese Patent Application No. 2012102933466 dated May 6, 2014, 5pgs.

(Continued)

*Primary Examiner* — Hoa Pham (57) ABSTRACT

A detect device and a detect method for transmittivity spectrum of the light guiding plate are provided. The detect device comprises a mixing cavity unit for providing a linear light source with continuous spectrum to a light guiding plate to be detected; a light guiding plate placing unit located at a side of the mixing cavity unit, on which the light guiding plate to be detected is disposed to receive light from the mixing cavity unit; and a detecting lens disposed above the light guiding plate placing unit for detect the spectrum.

15 Claims, 4 Drawing Sheets

(56) References Cited

U.S. PATENT DOCUMENTS

| | | | |
|---|---|---|---|
| 2002/0105638 A1* | 8/2002 | Kobayashi | 356/239.1 |
| 2004/0109058 A1* | 6/2004 | Katz | 348/14.04 |
| 2004/0109158 A1 | 6/2004 | Sung | |
| 2007/0171661 A1 | 7/2007 | Desvaud | |
| 2012/0033443 A1 | 2/2012 | Aho et al. | |

FOREIGN PATENT DOCUMENTS

| | | | |
|---|---|---|---|
| JP | 406294749 A | * | 10/1994 |
| JP | H06294749 A | | 10/1994 |
| JP | 2517368 | | 7/1996 |
| JP | H10274593 A | | 10/1998 |
| JP | 2005-049291 A | | 2/2005 |
| KR | 1020070056453 A | | 6/2007 |
| KR | 10-2011-0140112 A | | 12/2011 |
| TW | 200408837 | | 6/2004 |
| WO | 9427137 A2 | | 11/1994 |
| WO | 2009118952 A1 | | 10/2009 |

OTHER PUBLICATIONS

English translation of First Office Action issued by State Intellectual Property Office of the People's Republic of China for Chinese Patent Application No. 2012102933466 dated May 6, 2014, 5pgs.
Yi et al., Design of Low Power Consumption Backlight Unit for CCFL LCD TV, Chinese Journal of Liquid Crystals and Displays, Aug. 2011, pp. 480-485, vol. 26, No. 4.
European Patent Office Communication and European Search Report, issued Dec. 6, 2013, 13 pages.
English Translation of JPH06294749(A), 16 pages.
English Translation of KR1020070056453(A), 2 pages.
English Translation of JPH10274593(A), 13 pages.
Second Office Action issued by the State Intellectual Property Office of the People's Republic of China for Chinese Patent Application No. 2012102933466 dated Aug. 22, 2014, 7pgs.
English translation of Second Office Action issued by the State Intellectual Property Office of the People's Republic of China for Chinese Patent Application No. 2012102933466 dated Aug. 22, 2014, 6pgs.
Second Office Action issued by the Chinese Patent Office for Chinese Patent Application No. 201310240567.1 dated Aug. 18, 2014, 3pgs.
English translation of Second Office Action issued by the Chinese Patent Office for Chinese Patent Application No. 201310240567.1 dated Aug. 18, 2014, 2pgs.
Article in the Chinese language (cited as a reference in an Extended European Search Report previously submitted in the IDS of Jul. 11, 2014), titled Research on the Methods of Improving Uniformity and Brightness of the Backlight System, 62 pages.
English abstract of the article titled Research on the Methods of Improving Uniformity and Brightness of the Backlight System, 1 page.
Office Action issued by the Korean Patent Office in the corresponding Korean application No. 10-2013-0091548, 6 pgs.
English translation of Office Action issued by the Korean Patent Office in the corresponding Korean application No. 10-2013-0091548, 5 pgs.
English Abstract of JPH0290401A, published Mar. 29, 1990, 2 pages.
Office Action issued by the Korean Patent Office on Jan. 29, 2016 in the corresponding Korean application No. 10-2013-0091548, 4 pgs.
English translation of Office Action issued by the Korean Patent Office on Jan. 29, 2016 in the corresponding Korean application No. 10-2013-0091548, 3 pgs.
Korean Office Action issued by the Korean Patent Office in KR Application No. 10-2013-91548 dated Apr. 7, 2016 (pp. 5).
English translation of Korean Office Action issued by the Korean Patent Office in KR Application No. 10-2013-91548 dated Apr. 7, 2016 (pp. 3).
English language Abstract of KR10-2011-0140112 (pp. 1).
English language Abstract of JP2005049291 (pp. 1).

* cited by examiner

DEVICE AND A METHOD FOR DETECTING A TRANSMITTIVITY SPECTRUM OF A LIGHT GUIDING PLATE

CROSS REFERENCE TO RELATED APPLICATIONS

This application claims priority from Chinese National Application No. 201210293346.6, filed on Aug. 16, 2012, the contents of which are incorporated herein by reference.

BACKGROUND

The present invention relates to a method and a device for detecting a transmittivity spectrum of a light guiding plate.

With the rapid development of the display technology, liquid crystal display devices (such as liquid crystal TV sets, liquid crystal displays, liquid crystal display screens and the like) are increasingly widely used in manufacture and normal life due to it advantages of being driven with a low voltage, its flat panel structure, informative display, easy coloring, long life, no radiation and no pollution etc. However, liquid crystal display devices are display devices of a passive type, which can not emit light themselves and therefore have to modulate external light to achieve the object of displaying. Thus, backlights play a very important role in liquid crystal display devices.

Figure 1:
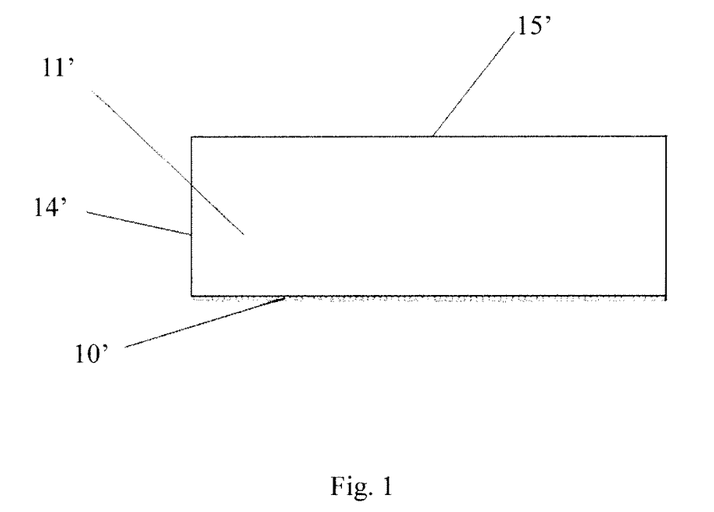
FIG. 1 is a structural schematic view of a light guiding plate of prior art.

A light guiding plate is one of the components which function importantly in a side light type backlight. FIG. 1 shows a structure schematic view of one example of a light guiding plate. The light guiding plate 11' is colorless and transparent, and its bottom surface forms as an optical functional surface 10'. At least one side of the light guiding plate 11' is designed as an incident surface 14'. Light from a light source enters into the light guiding plate 11' through the incident surface 14' and exits from an upper surface of the light guiding plate 11', i.e. an exiting surface 15' after a plurality of reflections by the optical functional surface 10' and an inner side of the light guiding plate to form a uniform surface light source.

Due to differences in light absorptivity of the material of the light guiding plate and the optical functional surface 10' for light with different wavelengths, and the like, the incident light of the incident surface 14' has a different spectrum from the exiting light of the exiting surface 15', which causes a chroma offset of the exiting light of the light guiding plate. If a spectrum of the light source is used to calculate directly, errors will be caused in the calculation result of the chroma of the liquid crystal display, thereby affecting product quality and production efficiency.

SUMMARY

One object of the invention is to provide a method and a device for detecting a transmittivity spectrum of a light guiding plate.

According to embodiments of the present invention, a device for detecting a transmittivity spectrum of a light guiding plate is provided, which comprises: a mixing cavity unit for providing a linear light source with continuous spectrum to a light guiding plate to be detected; a light guiding plate placing unit located at a side of the mixing cavity unit, on which the light guiding plate to be detected is placed to receive light from the mixing cavity unit; and a detecting lens disposed above the light guiding plate placing unit for detecting a spectrum.

The mixing cavity unit may comprise a mixing cavity case, a lamp reflection cover disposed within the mixing cavity case, and a standard light source disposed in the lamp reflection cover; and a light-passing slit is provided at a side of the mixing cavity case, through which the light from the standard light source passes to form the linear light source.

Preferably, the lamp reflection cover is consisted of a plurality of curved surface units, each having a vertical mid-splitting line that is a part of an ellipse and a horizontal mid-splitting line that is a part of a parabola, and the focus of the parabola of the horizontal mid-splitting line is coincident with a first focus of the two focuses of the ellipse of the vertical mid-splitting line. The standard light source may comprise a plurality of standard lamps, each being disposed on the first focus of the ellipse of the vertical mid-splitting line of one of the curved surface units. The light-passing slit passes through second focuses of the ellipses of the horizontal mid-splitting lines of the plurality of curved surface units of the lamp reflection cover.

Preferably, the plurality of standard lamps are connected in series.

Preferably, the mixing cavity unit further comprises an adjustable light-leaking slit disposed between the standard light source and the light-passing slit.

Preferably, the mixing cavity unit further comprises a light filter and a light homogenizer disposed between the standard light source and the adjustable light-leaking slit.

Preferably, the detecting lens can move horizontally between a position right above a center of the light guiding plate to be detected and a position right above the incident surface of the light guiding plate to be detected.

The light guiding plate placing unit can comprise a base, spacers and a reflecting sheet, the reflecting sheet being disposed on the base, the spacers being used to be selectively disposed between the reflecting sheet and the base, and the light guiding plate to be detected being disposed on the reflecting sheet.

Preferably, the base has an upper surface lower than the light-passing slit in the mixing cavity.

Preferably, the device further comprises a 45°-angled mirror for being disposed on the base to reflect the light from the light-passing slit into the detecting lens.

According to embodiments of the present invention, a method is further provided for detecting a transmittivity spectrum of the light guiding plate using a device for detecting a transmittivity spectrum of a light guiding plate. The device for detecting a transmittivity spectrum of a light guiding plate comprises a mixing cavity unit for providing a linear light source with continuous spectrum to a light guiding plate to be detected; a light guiding plate placing unit located at a side of the mixing cavity unit, on which the light guiding plate to be detected is placed to receive light from the mixing cavity unit; and a detecting lens disposed above the light guiding plate placing unit for detect the spectrum. The method comprises: measuring an exiting light spectrum of the light guiding plate; measuring an incident light spectrum of the light guiding plate; and calculating a transmittivity spectrum of the light guiding plate: the transmittivity spectrum of the light guiding plate=the exiting light spectrum/the incident light spectrum.

Preferably, the light guiding plate placing unit comprises a base, spacers and a reflecting sheet, and said measuring the exiting light spectrum of the light guiding plate comprising: selecting spacers, and disposing the spacers, the reflecting sheet and a light guiding plate to be detected on the base in this order to make the incident surface of the light guiding plate to be detected corresponding to a light-passing slit in the mixing cavity unit.

Preferably, the mixing cavity unit of the device for detecting a transmittivity spectrum of a light guiding plate has an adjustable light-leaking slit; and said measuring the exiting light spectrum of the light guiding plate comprises adjusting a width of the adjustable light-leaking slit according to a thickness of the light guiding plate to be detected, to make it smaller than the thickness of the light guiding plate to be detected.

Preferably, said measuring the exiting light spectrum of the light guiding plate is performed when the detecting lens is located right above a center of the light guiding plate to be detected.

Preferably, said measuring the incident light spectrum of the light guiding plate comprises: controlling a state of the mixing cavity unit to be the same as that when measuring exiting light spectrum; disposing a 45°-angled mirror on the light guiding plate placing unit to reflect the light from the light-passing slit of the mixing cavity unit upwardly; and moving the detecting lens to focus on an image of the light-leaking slit reflected by the mirror, and reading the incident light spectrum.

Preferably, the mirror is disposed in a position where the incident surface of the light guiding plate to be detected is located when the exiting light spectrum of the light guiding plate is measured.

BRIEF DESCRIPTION OF THE DRAWINGS

In order to clearly illustrate the technical solution of the embodiments of the invention, the drawings of the embodiments will be briefly described below; and it is obvious that the described drawings are only related to some embodiments of the invention and thus are not limitative of the invention.

REFERENCE NUMERALS

1: standard light source; 2: lamp reflection cover; 3: mixing cavity unit; 4: light filter; 5: light homogenizer; 6: adjustable light-leaking slit; 7: light-passing slit; 8: base; 9: spacer; 10: reflecting sheet; 11: light guiding plate to be detected; 12: detecting lens; 13: mirror; 14: incident surface; 15: exiting surface; 16: lamp reflection case.

DETAILED DESCRIPTION

In order to make objects, technical details and advantages of the embodiments of the invention apparent, the technical solutions of the embodiment will be described in a clearly and fully understandable way in connection with the drawings related to the embodiments of the invention. It is obvious that the described embodiments are just a part but not all of the embodiments of the invention. Based on the described embodiments herein, those skilled in the art can obtain other embodiment(s), without any inventive work, which should be within the scope of the invention.

Figure 2:
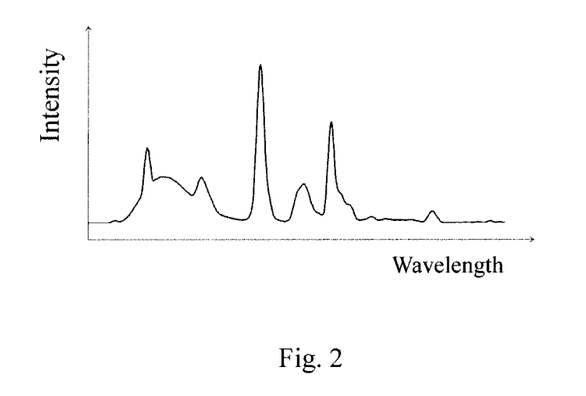
FIG. 2 is a schematic view of a spectrum of a cold cathode fluorescent lamp.
Figure 3:
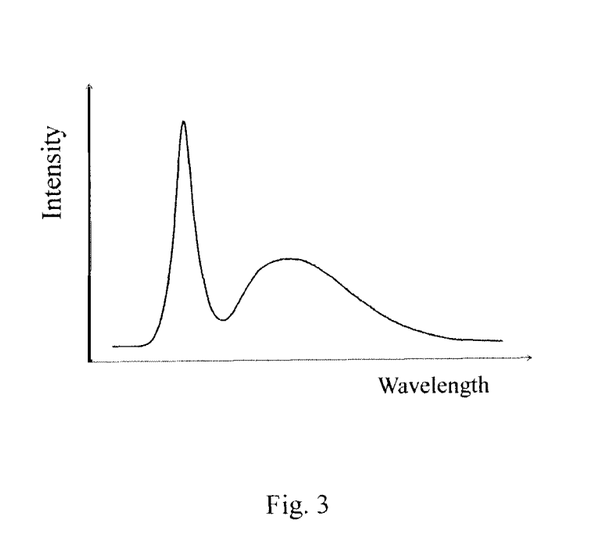
FIG. 3 is a schematic view of a spectrum of a white LED (light-emittig diode)

A backlight in a liquid crystal display usually uses a cold cathode fluorescent lamp or a white light LED (light-emitting diode) as a light source. FIG. 2 and FIG. 3 show the spectrums of a cold cathode fluorescent lamp and a white light LED, respectively. It can be seen from the figures that the spectrums of the two light sources are both discontinuous. If these two light sources are used to carry out detection, then a relatively big error would occur at a wavelength with a relatively small intensity (i.e. the regions with small vertical coordinates in FIG. 2 and FIG. 3).

Figure 4:
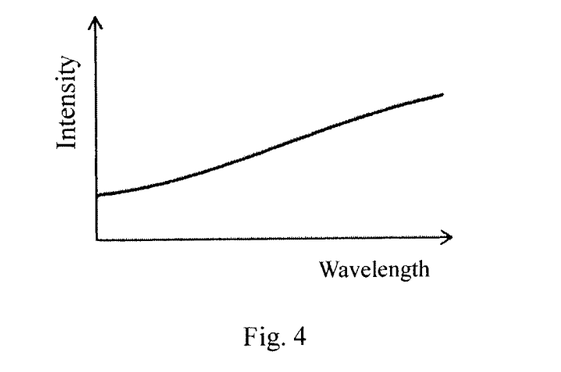
FIG. 4 is a schematic view of a spectrum of the standard light source in the mixing cavity unit in the device for detecting a transmittivity spectrum of a light guiding plate according to an embodiment of the invention.

FIG. 4 shows a spectrum of a standard light source. It can be seen from the figure that the spectrum of the standard light source is continuous. A complete spectrum of the transmittivity of a light guiding plate at different wavelengths can be measured only when a continuous spectrum is used as a light source illuminating light guiding plate. However, since the light guiding plate usually has a small thickness of about 0.4 mm~4 mm in a side light type backlight of a liquid crystal display, it is difficult to detect with a standard light source having a matching size.

In embodiments of the present invention, a mixing cavity of a particular structure is used to generate a linear light source which has uniform brightness, a continuous spectrum, and a size which is adapted to the size of the light guiding plate of the side light type backlight of the liquid crystal display, for detecting of the transmittivity spectrum of the light guiding plate, which solves the technical problem that the transmittivity spectrum of the light guiding plate can not be detected.

FIGS. 5-8 show a device for detecting a transmittivity spectrum of the light guiding plate provided according to the embodiment of the invention, the detect device comprising:

a mixing cavity unit 3 for providing a linear light source which has uniform brightness and a continuous spectrum to a light guiding plate to be detected 11; and a light guiding plate placing unit located at a side of the mixing cavity unit 3, on which the light guiding plate to be detected is disposed to receive light from the mixing cavity unit; and a detecting lens 12 disposed above the light guiding plate placing unit for detecting the spectrum.

The device for detecting a transmittivity spectrum of a light guiding plate according to the embodiment of the invention has a simple structure, is easy to operate, and calculates the transmittivity spectrum of the light guiding plate of a side light type by measuring the incident light spectrum and the exiting light spectrum of the light guiding plate, so as to provide references for design and quality control of the backlight.

Figure 5:
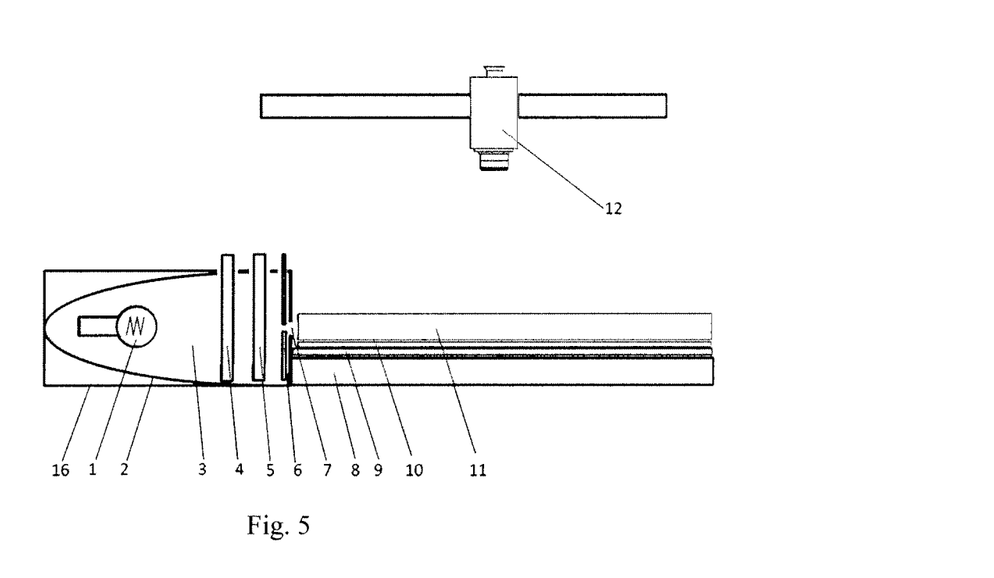
FIG. 5 is a schematic view of the device for detecting a transmittivity spectrum of a light guiding plate according to the embodiment of the invention, showing a state of detecting an exiting light spectrum of a light guiding plate.
Figure 6:
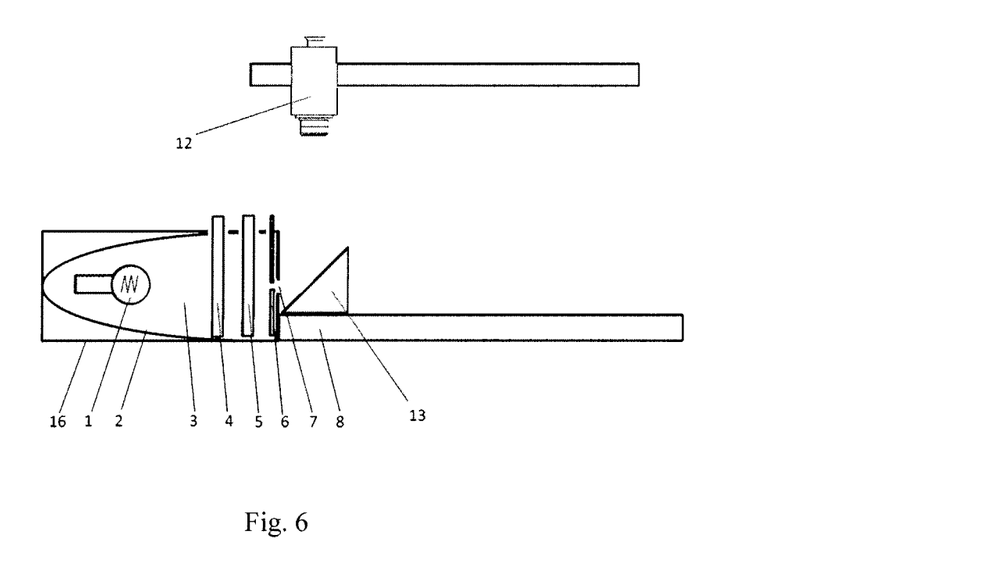
FIG. 6 is a schematic view of the device for detecting a transmittivity spectrum of a light guiding plate according to the embodiment of the invention, showing a state of detecting an incident light spectrum of a light guiding plate.

As shown in FIG. 5 and FIG. 6, the mixing cavity unit 3 comprises: a mixing cavity case 16, a lamp reflection cover 2 disposed in the mixing cavity case 16, and a standard light source 1 disposed in the lamp reflection cover 2. In addition, a light-passing slit 7 is disposed at a side of the mixing cavity case 16, through which the light of the standard light source 1 passes to form a linear light source.

In preferred embodiments of the invention, the lamp reflection cover 2 is consisted of a plurality of curved surface units, each having a vertical mid-splitting line that is a part of an ellipse and a horizontal mid-splitting line that is a part of a parabola. The focus of the parabola of the horizontal mid-splitting line is coincident with a first focus of the two focus of the ellipse of the vertical mid-splitting line.

Figure 7:
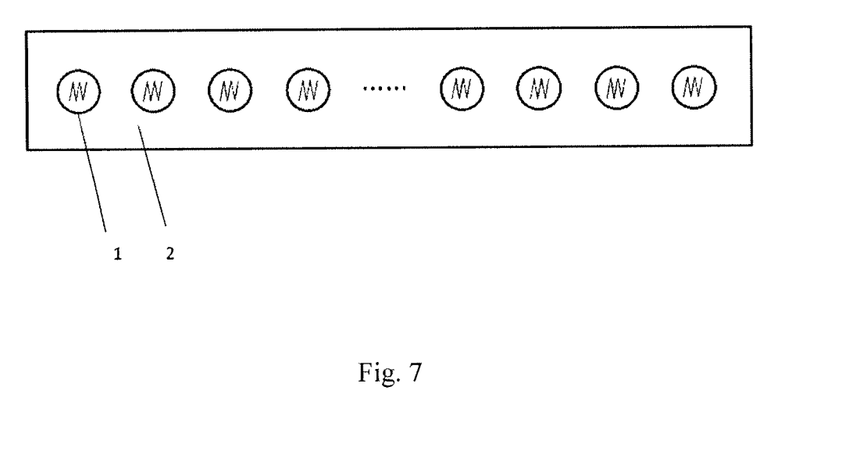
FIG. 7 is a schematic view of the disposition of the standard light source in the device for detecting a transmittivity spectrum of the light guiding plate of embodiment of the invention.
Figure 8:
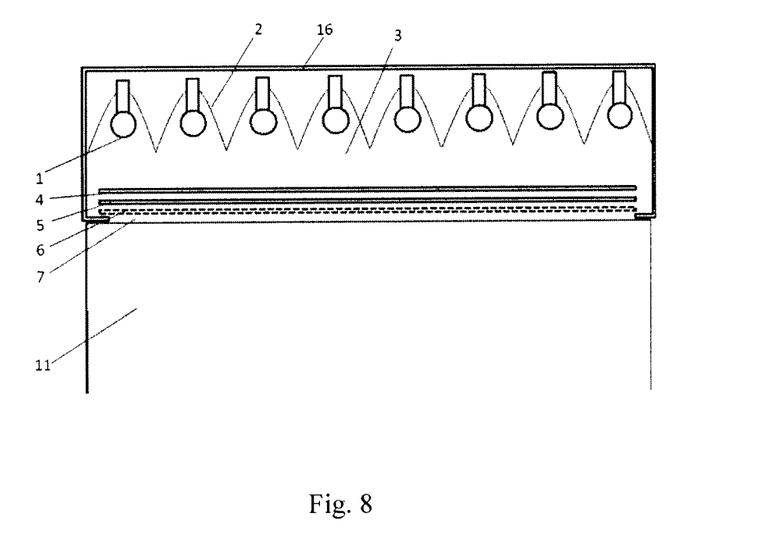
FIG. 8 is a partial top view of the device for detecting a transmittivity spectrum of the light guiding plate according to the embodiment of the invention, with the mixing cavity unit shown in a cross section.

As shown in FIGS. 7 and 8, the standard light source 1 comprises a plurality of standard lamps. Each of the standard lamps is preferably disposed on the first focus of the ellipse of the vertical mid-splitting line of one of the curved surface units. The light-passing slit 7 passes through second focuses of the ellipses of the vertical mid-splitting lines of the plurality of the curved surface units of the lamp reflection cover. This enables the light from the standard light source to converge at the light-passing slit 7 again and to illuminate the incident surface of the light guiding plate to be detected effectively.

The plurality of standard lamps may be connected in series. This may help to improve uniformity of the light.

A light filter 4, a light homogenizer 5 and an adjustable light-leaking slit 6 may be disposed in this order between the standard light source 1 and the light-passing slit 7. The light filter 4 functions to filter the spectrum of the standard light source 1 to select a spectrum with particular band to detect, so as to precisely detect the transmittivity spectrum of the light guiding plate with different bands. The light homogenizer 5 functions to homogenize the light in the horizontal direction to make the light bar composed of the plurality of standard lamps have uniform brightness in the horizontal direction, avoiding the alternation of brightness and darkness within the light guiding plate to be detected 11, so as to enhance the precision of the detection. The adjustable light-leaking slit 6 functions to make the width of light from the light-passing slit 7 adjustable by replacing the light-leaking slit with another slit having a different width so as to match light guiding plates to be detected 11 with different thickness.

In preferred embodiments of the present invention, the light guiding plate placing unit is constructed to enable alignment of exiting surfaces of light guiding plates having different thicknesses with the light-passing slit to ensure sufficient incident efficiency. As shown in figures, the light guiding plate placing unit is composed of a base 8, spacers 9 (only one of them is shown), and a reflecting sheet 10. The base 8 has a structure with a certain height and a flattened surface, which has an upper surface slightly lower than the light-passing slit 7 in the mixing cavity unit 3. Disposing the spacers 9 of different heights on the base 8 enables flushing middle planes of light guiding plates with different thicknesses with a central plane of the light-passing slit 7 to achieve the best incident efficiency. The reflecting sheet 10, which functions the same as the reflecting sheet in the backlight of the liquid crystal display, is disposed on the spacer 9. The light guiding plate to be detected 11 is disposed on the reflecting sheet 10, and the exiting surface of the light guiding plate to be detected 11 faces upward and its incident surface is corresponding to the light-passing slit 7 of the mixing cavity 3.

It should be noted that the spacer 9 may not be disposed between the base 8 and the reflecting sheet 10 as required.

The detecting lens 12 is located right above the light guiding plate to be detected 11, and preferably can move horizontally between a position right above a center of the light guiding plate to be detected 11 and a position right above the incident surface of the light guiding plate to be detected 11.

The device for detecting a transmittivity spectrum of a light guiding plate provided by the invention has a simple structure, is easy to operate, and uses a standard illuminant as the light source, which is adjusted by the reflecting sheet and the light-passing slit to be the linear light source so as to enter a light guiding plate of the side light type, and in the device, the transmittivity spectrum of the side light type light guiding plate is calculated based on the measurements of the incident light spectrum and the exiting light spectrum of light guiding plate, so as to provide references for design and quality control of backlights.

According to embodiments of the invention, a method for detecting a transmittivity spectrum of the light guiding plate is also provided, which uses the detect device described above. The method comprising:

measuring an exiting light spectrum of the light guiding plate;

measuring an incident light spectrum of the light guiding plate; and calculating the transmittivity spectrum of the light guiding plate: the transmittivity spectrum of the light guiding plate=the exiting light spectrum/the incident light spectrum.

The method for detecting a transmittivity spectrum of the light guiding plate provided by the invention is easy to operate, uses a standard illuminant as the light source, in which the light source is adjusted by the reflecting sheet and the light-passing slit to be a linear light source so as to enter a light guiding plate of the side light type, and the transmittivity spectrum of the light guiding plate of the side light type is calculated based on the measurements of the incident light spectrum and the exiting light spectrum of the light guiding plate, so as to provide references for design and quality control of backlights.

With reference to FIG. 5, measuring the exiting light spectrum of the light guiding plate may comprises selecting spacers, and disposing a light guiding plate to be detected 11, the spacers 9 and a reflecting sheet 10 on a base 8 in this order to make the incident surface of the light guiding plate to be detected 11 correspond to the light-passing slit 7 in the mixing cavity.

Measuring the exiting light spectrum of the light guiding plate may also comprises adjusting a width of an adjustable light-leaking slit 6 according to the thickness of the light guiding plate to be detected to make the width of the light-leaking slit smaller than the thickness of the light guiding plate.

In addition, preferably measuring the exiting light spectrum of the light guiding plate is performed when the detecting lens is located right above the center of the light guiding plate to be detected.

With reference to FIG. 6, measuring the incident light spectrum of the light guiding plate may comprise:

After the exiting light spectrum detect is finished, keeping the state of the mixing cavity unit unchanged and removing the spacers, the reflecting sheet and the light guiding plate to be detected; mounting a 45°-angled mirror; and moving the detecting lens to image by aligning the light-leaking slit reflected from within the mirror, and reading the incident light spectrum.

Since the light from the light-leaking slit is in horizontal direction whereas the detecting lens is in vertical direction, the detecting lens can not directly receive the light from the light-leaking slit. Therefore, it is required to mount a 45°-angled mirror to reflect the light into the lens. During detect, all need is to align the detecting lens to the image in the mirror to perform the detection.

The method for detecting a transmittivity spectrum of a light guiding plate provided according to embodiments of the present invention is easy to operate, and uses a standard illuminant as the light source, in which the light source is adjusted by the reflecting sheet and the light-passing slit to be a linear light source so as to enter the side light type light guiding plate, and the transmittivity spectrum of the light guiding plate of the side light type is calculated based on measurements of the incident light spectrum and the exiting light spectrum of light guiding plate, so as to provide references for the design and quality control of the backlight.

Although the embodiments of the invention have been described above, it will be obvious that the same may be varied in many ways. Such variations are not to be regarded as a departure from the spirit and scope of the invention, and all such modifications as would be obvious to those skilled in the art are intended to be included within the scope of the following claims.

What is claimed is:

1. A device for detecting a transmittivity spectrum of a light guiding plate, comprising:
   a mixing cavity unit for providing a linear light source with continuous spectrum to a light guiding plate to be detected;
   a light guiding plate placing unit, on which the light guiding plate to be detected is placed to receive light from the mixing cavity unit; and
   a detecting lens disposed above the light guiding plate placing unit for detecting a spectrum;
   wherein the mixing cavity unit is located at a side of the light guiding plate placing unit substantially in a same plane, and comprises a mixing cavity case, a lamp reflection cover disposed within the mixing cavity case, and a standard light source disposed in the lamp reflection cover; the mixing cavity case comprises an opening facing the light guiding plate placing unit; a light-passing slit is provided at the opening of the mixing cavity case, the light-passing slit is narrower than the opening of the mixing cavity case, and through the light-passing slit the light from the standard light source passes to form the linear light source;
   wherein the mixing cavity unit further comprises a light homogenizer disposed between the standard light source and the light-passing slit, the light homogenizer configured to homogenize the light from the standard light source to have uniform brightness in a horizontal direction.

2. The device for detecting a transmittivity spectrum of a light guiding plate according to claim 1, wherein
   the lamp reflection cover includes a plurality of curved surface units, each having a vertical mid-splitting line that is a part of an ellipse and a horizontal mid-splitting line that is a part of a parabola, and the focus of the parabola of the horizontal mid-splitting line is coincident with a first focus of the two focuses of the ellipse of the vertical mid-splitting line;
   the standard light source comprises a plurality of standard lamps, each being disposed on the first focus of the ellipse of the vertical mid-splitting line of one of the curved surface units; and
   the light-passing slit passes through second focuses of the ellipses of the horizontal mid-splitting lines of the plurality of curved surface units of the lamp reflection cover.

3. The device for detecting a transmittivity spectrum of a light guiding plate according to claim 2, wherein the plurality of standard lamps are connected in series.

4. The device for detecting a transmittivity spectrum of a light guiding plate according to claim 2, wherein the mixing cavity unit further comprises an adjustable light-leaking slit disposed between the light homogenizer and the light-passing slit.

5. The device for detecting a transmittivity spectrum of a light guiding plate according to claim 4, wherein the mixing cavity unit further comprises a light filter disposed between the standard light source and the light homogenizer.

6. The device for detecting a transmittivity spectrum of a light guiding plate according to claim 2, wherein the light guiding plate placing unit comprises a base, spacers and a reflecting sheet, the reflecting sheet being disposed on the base, the spacers being used to be selectively disposed between the reflecting sheet and the base, and the light guiding plate to be detected being disposed on the reflecting sheet.

7. The device for detecting a transmittivity spectrum of a light guiding plate according to claim 6, wherein the base has an upper surface lower than the light-passing slit in the mixing cavity.

8. The device for detecting a transmittivity spectrum of a light guiding plate according to claim 1, wherein the detecting lens can move horizontally between a position right above a center of the light guiding plate to be detected and a position right above the incident surface of the light guiding plate to be detected.

9. The device for detecting a transmittivity spectrum of a light guiding plate according to claim 1, further comprising a 45°-angled mirror for being disposed on the base to reflect the light from the light-passing slit into the detecting lens.

10. A method for detecting a transmittivity spectrum of the light guiding plate using a device for detecting a transmittivity spectrum of a light guiding plate, the device for detecting a transmittivity spectrum of a light guiding plate comprising a mixing cavity unit for providing a linear light source with continuous spectrum to a light guiding plate to be detected; a light guiding plate placing unit, on which the light guiding plate to be detected is placed to receive light from the mixing cavity unit; and a detecting lens disposed above the light guiding plate placing unit for detect the spectrum;
   wherein the mixing cavity unit is located at a side of the light guiding plate placing unit substantially in a same plane, and comprises a mixing cavity case, a lamp reflection cover disposed within the mixing cavity case, and a standard light source disposed in the lamp reflection cover; the mixing cavity case comprises an opening facing the light guiding plate placing unit; a light-passing slit is provided at the opening of the mixing cavity case, the light-passing slit is narrower than the opening of the mixing cavity case, and through the light-passing slit the light from the standard light source passes to form the linear light source;
   wherein the mixing cavity unit further comprises a light homogenizer disposed between the standard light source and the light-passing slit, the light homogenizer configured to homogenize the light from the standard light source to have uniform brightness in a horizontal direction; and wherein the method comprises:
measuring an exiting light spectrum of the light guiding plate;
measuring an incident light spectrum of the light guiding plate; and
calculating a transmittivity spectrum of the light guiding plate: the transmittivity spectrum of the light guiding plate=the exiting light spectrum/the incident light spectrum.

11. The method according to claim 10, wherein the light guiding plate placing unit comprises a base, spacers and a reflecting sheet, said measuring the exiting light spectrum of the light guiding plate comprising:
selecting spacers, and disposing the spacers, the reflecting sheet and a light guiding plate to be detected on the base in this order to make the incident surface of the light guiding plate to be detected corresponding to the light-passing slit in the mixing cavity unit.

12. The method according to claim 10, wherein the mixing cavity unit of the device for detecting a transmittivity spectrum of a light guiding plate has an adjustable light-leaking slit; and
said measuring the exiting light spectrum of the light guiding plate comprises adjusting a width of the adjustable light-leaking slit according to a thickness of the light guiding plate to be detected, to make it smaller than the thickness of the light guiding plate to be detected.

13. The method according to claim 10, wherein said measuring the exiting light spectrum of the light guiding plate is performed when the detecting lens is located right above a center of the light guiding plate to be detected.

14. The method according to claim 10, wherein said measuring the incident light spectrum of the light guiding plate comprises:
controlling a state of the mixing cavity unit to be the same as that when measuring exiting light spectrum;
disposing a 45°-angled mirror on the light guiding plate placing unit to reflect the light from the light-passing slit of the mixing cavity unit upwardly; and
moving the detecting lens to focus on an image of the light-leaking slit reflected by the mirror, and reading the incident light spectrum.

15. The method according to claim 14, wherein the mirror is disposed in a position where the incident surface of the light guiding plate to be detected is located when the exiting light spectrum of the light guiding plate is measured.

* * * * *